US008721713B2

(12) United States Patent
Tower et al.

(10) Patent No.: US 8,721,713 B2
(45) Date of Patent: May 13, 2014

(54) SYSTEM FOR IMPLANTING A REPLACEMENT VALVE

(75) Inventors: Allen J. Tower, North Lawrence, NY (US); Philipp Bonhoeffer, Paris (FR); Michael L. Martin, Nicholville, NY (US)

(73) Assignee: Medtronic, Inc., Minneapolis, MN (US)

( * ) Notice: Subject to any disclaimer, the term of this patent is extended or adjusted under 35 U.S.C. 154(b) by 1294 days.

(21) Appl. No.: 10/127,969

(22) Filed: Apr. 23, 2002

(65) Prior Publication Data
US 2003/0199963 A1     Oct. 23, 2003

(51) Int. Cl.
*A61M 25/01*     (2006.01)

(52) U.S. Cl.
USPC ........................................ 623/2.11

(58) Field of Classification Search
USPC ........... 623/1.11, 1.13, 1.14, 1.24, 1.25, 1.12, 623/1.23, 2.11; 606/194, 108; 604/103.05, 604/103.09, 104, 194; 60/104, 194, 103.05, 60/103.09; 624/1.24, 1.25, 1.13, 1.14
See application file for complete search history.

(56) References Cited

U.S. PATENT DOCUMENTS

| | | | |
|---|---|---|---|
| 3,409,013 A | 11/1968 | Berry | |
| 3,587,115 A | 6/1971 | Shiley | |
| 3,714,671 A | 2/1973 | Edwards et al. | |
| 3,755,823 A | 9/1973 | Hancock | |
| 4,035,849 A | 7/1977 | Angell et al. | |
| 4,222,126 A | 9/1980 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,470,157 A | 9/1984 | Love | |
| 4,574,803 A | 3/1986 | Storz | |
| 4,592,340 A | 6/1986 | Boyles | |

(Continued)

FOREIGN PATENT DOCUMENTS

| | | |
|---|---|---|
| DE | 36 40 745 | 6/1987 |
| DE | 195 32 846 | 3/1997 |

(Continued)

OTHER PUBLICATIONS

Younes Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

(Continued)

*Primary Examiner* — Ryan Severson

(57) ABSTRACT

A system for percutaneously inserting a prosthesis containing a biological replacement for a defective valve into an implantation site through a body lumen. The system contains a balloon catheter upon which a collapsable stent containing a venous valvular replacement is mounted. A protective shield is slidably mounted upon the catheter that is movable between a closed position over the balloon and an open position wherein the balloon can be inflated to expand the stent. A central lumen runs through the catheter that is formed of stainless steel. The central lumen provides a one to one torque ratio between the proximal end of the catheter and the distal end to enhance the steerability of the catheter. The vein of the replacement is reduced in thickness between 50% and 90% of its original size thereby considerably reducing the size of the replacement package when the stem is collapsed upon the balloon of the catheter.

10 Claims, 2 Drawing Sheets

(56) References Cited

U.S. PATENT DOCUMENTS

| | | | |
|---|---|---|---|
| 4,612,011 A | 9/1986 | Kautzky | |
| 4,681,110 A | 7/1987 | Wiktor | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,967,743 A * | 11/1990 | Lambert | 604/905 |
| 4,979,939 A | 12/1990 | Shiber | |
| 4,986,830 A | 1/1991 | Owens et al. | |
| 5,007,896 A | 4/1991 | Shiber | |
| 5,026,366 A | 6/1991 | Leckrone | |
| 5,047,041 A | 9/1991 | Samuels | |
| 5,059,177 A | 10/1991 | Towne et al. | |
| 5,061,273 A | 10/1991 | Yock | |
| 5,085,635 A | 2/1992 | Cragg | |
| 5,089,015 A | 2/1992 | Ross | |
| 5,152,771 A | 10/1992 | Sabbaghian et al. | |
| 5,167,628 A | 12/1992 | Boyles | |
| 5,232,445 A | 8/1993 | Bonzel | |
| 5,257,979 A * | 11/1993 | Jagpal | 604/104 |
| 5,272,909 A | 12/1993 | Nguyen et al. | |
| 5,295,958 A | 3/1994 | Shturman | |
| 5,327,774 A | 7/1994 | Nguyen et al. | |
| 5,338,313 A | 8/1994 | Mollenauer et al. | |
| 5,429,597 A * | 7/1995 | DeMello et al. | 606/194 |
| 5,443,446 A | 8/1995 | Shturman | |
| 5,449,372 A * | 9/1995 | Schmaltz et al. | 606/198 |
| 5,480,424 A | 1/1996 | Cox | |
| 5,496,346 A | 3/1996 | Horzewski et al. | |
| 5,500,014 A | 3/1996 | Quijano et al. | |
| 5,514,109 A | 5/1996 | Mollenauer et al. | |
| 5,545,209 A | 8/1996 | Roberts et al. | |
| 5,556,387 A | 9/1996 | Mollenauer et al. | |
| 5,580,922 A | 12/1996 | Park et al. | |
| 5,591,195 A | 1/1997 | Taheri et al. | |
| 5,597,378 A | 1/1997 | Jervis | |
| 5,609,626 A | 3/1997 | Quijano et al. | |
| 5,643,278 A * | 7/1997 | Wijay | 623/1.11 |
| 5,683,451 A | 11/1997 | Lenker et al. | |
| 5,702,368 A | 12/1997 | Stevens et al. | |
| 5,749,890 A | 5/1998 | Shaknovich | |
| 5,749,921 A | 5/1998 | Lenker et al. | |
| 5,782,809 A | 7/1998 | Umeno et al. | |
| 5,824,041 A | 10/1998 | Lenker et al. | |
| 5,824,061 A | 10/1998 | Quijano et al. | |
| 5,840,081 A | 11/1998 | Andersen et al. | |
| 5,855,601 A | 1/1999 | Bessler et al. | |
| 5,906,606 A * | 5/1999 | Chee et al. | 604/527 |
| 5,906,619 A | 5/1999 | Olson et al. | |
| 5,957,949 A * | 9/1999 | Leonhardt et al. | 623/1.24 |
| 5,968,068 A | 10/1999 | Dehdashtian et al. | |
| 5,997,573 A | 12/1999 | Quijano et al. | |
| 6,022,370 A | 2/2000 | Tower | |
| 6,042,589 A | 3/2000 | Marianne | |
| 6,059,809 A | 5/2000 | Amor et al. | |
| 6,110,201 A | 8/2000 | Quijano et al. | |
| 6,117,166 A * | 9/2000 | Winston et al. | 623/1.13 |
| 6,123,723 A * | 9/2000 | Konya et al. | 623/1.11 |
| 6,162,208 A | 12/2000 | Hipps | |
| 6,171,335 B1 | 1/2001 | Wheatley et al. | |
| 6,203,550 B1 | 3/2001 | Olson | |
| 6,245,102 B1 * | 6/2001 | Jayaraman | 623/1.15 |
| 6,254,564 B1 * | 7/2001 | Wilk et al. | 623/1.24 |
| 6,287,315 B1 | 9/2001 | Wijeratne et al. | |
| 6,299,637 B1 | 10/2001 | Shaolia et al. | |
| 6,302,906 B1 | 10/2001 | Goicoechea et al. | |
| 6,319,281 B1 * | 11/2001 | Patel | 623/2.3 |
| 6,338,725 B1 | 1/2002 | Hermann et al. | |
| 6,350,278 B1 | 2/2002 | Lenker et al. | |
| 6,355,027 B1 * | 3/2002 | Le et al. | 604/525 |
| 6,355,060 B1 | 3/2002 | Lenker et al. | |
| 6,380,457 B1 | 4/2002 | Yurek et al. | |
| 6,454,799 B1 * | 9/2002 | Schreck | 623/2.18 |
| 6,461,382 B1 | 10/2002 | Cao | |
| 6,569,196 B1 | 5/2003 | Vesely | |
| 6,572,645 B2 | 6/2003 | Leonhardt | |
| 6,605,112 B1 | 8/2003 | Moll et al. | |
| 6,656,213 B2 | 12/2003 | Solem | |
| 6,786,925 B1 | 9/2004 | Schoon | |
| 6,790,229 B1 | 9/2004 | Berreklouw | |
| 6,797,002 B2 | 9/2004 | Spence | |
| 6,821,297 B2 | 11/2004 | Snyders | |
| 6,830,584 B1 | 12/2004 | Seguin | |
| 6,830,585 B1 | 12/2004 | Artof | |
| 6,852,116 B2 | 2/2005 | Leonhardt et al. | |
| 6,866,650 B2 | 3/2005 | Stevens | |
| 6,872,223 B2 | 3/2005 | Roberts | |
| 6,878,161 B2 | 4/2005 | Lenker | |
| 6,893,460 B2 | 5/2005 | Spenser et al. | |
| 6,908,481 B2 | 6/2005 | Cribier | |
| 6,911,039 B2 | 6/2005 | Shiu et al. | |
| 6,945,990 B2 | 9/2005 | Greenan | |
| 6,951,571 B1 | 10/2005 | Srivastava | |
| 6,974,474 B2 | 12/2005 | Pavcnik et al. | |
| 6,986,774 B2 | 1/2006 | Middleman et al. | |
| 6,989,028 B2 | 1/2006 | Lashinski et al. | |
| 7,060,038 B2 | 6/2006 | Letort et al. | |
| 7,105,016 B2 | 9/2006 | Shiu et al. | |
| 7,115,141 B2 | 10/2006 | Menz et al. | |
| 7,128,759 B2 | 10/2006 | Osborne et al. | |
| 7,147,663 B1 | 12/2006 | Berg et al. | |
| 7,153,324 B2 | 12/2006 | Case et al. | |
| 7,163,552 B2 | 1/2007 | Diaz | |
| 7,264,632 B2 | 9/2007 | Wright et al. | |
| 2001/0002445 A1 | 5/2001 | Vesely | |
| 2001/0007956 A1 | 7/2001 | Letac et al. | |
| 2002/0029014 A1 | 3/2002 | Jayaraman | |
| 2002/0032481 A1 | 3/2002 | Gabbay | |
| 2002/0072789 A1 | 6/2002 | Hackett et al. | |
| 2002/0138138 A1 | 9/2002 | Yang | |
| 2003/0036791 A1 | 2/2003 | Philipp et al. | |
| 2003/0050694 A1 | 3/2003 | Yang et al. | |
| 2003/0065386 A1 | 4/2003 | Weadock | |
| 2003/0069492 A1 | 4/2003 | Abrams et al. | |
| 2003/0199963 A1 | 10/2003 | Tower et al. | |
| 2003/0199971 A1 | 10/2003 | Tower et al. | |
| 2003/0212410 A1 | 11/2003 | Stenzel et al. | |
| 2004/0093005 A1 | 5/2004 | Durcan | |
| 2004/0093060 A1 | 5/2004 | Sequin et al. | |
| 2004/0097788 A1 | 5/2004 | Mourles et al. | |
| 2004/0111096 A1 | 6/2004 | Tu | |
| 2004/0122516 A1 | 6/2004 | Fogarty | |
| 2004/0148008 A1 | 7/2004 | Goodson, IV | |
| 2004/0167573 A1 | 8/2004 | Williamson | |
| 2004/0167620 A1 | 8/2004 | Ortiz | |
| 2004/0193261 A1 | 9/2004 | Berreklouw | |
| 2004/0210304 A1 | 10/2004 | Seguin et al. | |
| 2004/0210307 A1 | 10/2004 | Khairkhahan | |
| 2004/0215333 A1 | 10/2004 | Duran | |
| 2004/0225353 A1 | 11/2004 | McGuckin, Jr. | |
| 2004/0225354 A1 | 11/2004 | Allen | |
| 2004/0254636 A1 | 12/2004 | Flagle et al. | |
| 2004/0260394 A1 | 12/2004 | Douk et al. | |
| 2005/0010287 A1 | 1/2005 | Macoviak | |
| 2005/0033398 A1 | 2/2005 | Seguin | |
| 2005/0043790 A1 | 2/2005 | Seguin | |
| 2005/0049692 A1 | 3/2005 | Numamoto | |
| 2005/0049696 A1 | 3/2005 | Siess | |
| 2005/0060029 A1 | 3/2005 | Le | |
| 2005/0075584 A1 | 4/2005 | Cali | |
| 2005/0075712 A1 | 4/2005 | Biancucci | |
| 2005/0075717 A1 | 4/2005 | Nguyen | |
| 2005/0075719 A1 | 4/2005 | Bergheim | |
| 2005/0075724 A1 | 4/2005 | Svanidze | |
| 2005/0075730 A1 | 4/2005 | Myers | |
| 2005/0075731 A1 | 4/2005 | Artof | |
| 2005/0096736 A1 | 5/2005 | Osse et al. | |
| 2005/0107871 A1 | 5/2005 | Realyvasquez et al. | |
| 2005/0113910 A1 | 5/2005 | Paniagua | |

(56) References Cited

U.S. PATENT DOCUMENTS

| | | |
|---|---|---|
| 2005/0131438 A1 | 6/2005 | Cohn |
| 2005/0137686 A1 | 6/2005 | Salahieh |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0187616 A1 | 8/2005 | Realyvasquez |
| 2005/0203549 A1 | 9/2005 | Realyvasquez |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2006/0004439 A1 | 1/2006 | Spenser et al. |
| 2006/0009841 A1 | 1/2006 | McGuckin et al. |
| 2006/0020319 A1 | 1/2006 | Kim et al. |
| 2006/0259134 A1 | 11/2006 | Schwammenthal et al. |
| 2007/0005131 A1 | 1/2007 | Taylor |
| 2007/0016286 A1 | 1/2007 | Herrmann et al. |
| 2007/0043420 A1 | 2/2007 | Lostetter |
| 2007/0088431 A1 | 4/2007 | Bourang |
| 2008/0114442 A1 | 5/2008 | Mitchell et al. |
| 2008/0228170 A1 | 9/2008 | Murray |
| 2008/0228255 A1 | 9/2008 | Rust et al. |
| 2008/0255652 A1 | 10/2008 | Thomas et al. |
| 2008/0262590 A1 | 10/2008 | Murray |
| 2008/0262596 A1 | 10/2008 | Xiao |
| 2008/0262597 A1 | 10/2008 | Xiao |

FOREIGN PATENT DOCUMENTS

| | | |
|---|---|---|
| DE | 195 46 692 | 6/1997 |
| DE | 195 46 692 C2 | 6/1997 |
| DE | 198 57 887 | 7/2000 |
| DE | 199 07 646 | 8/2000 |
| DE | 100 49 812 | 4/2002 |
| DE | 100 49 813 | 4/2002 |
| DE | 100 49 814 | 4/2002 |
| DE | 100 49 815 | 4/2002 |
| EP | 0 597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1472996 | 11/2004 |
| FR | 2788217 | 12/1999 |
| GB | 1 268 484 | 3/1972 |
| GB | 2056023 | 3/1981 |
| SU | 1271508 | 11/1986 |
| SU | 1371700 | 2/1988 |
| WO | 91-17720 | 11/1991 |
| WO | 92-17118 | 10/1992 |
| WO | 93-01768 | 2/1993 |
| WO | 98/14137 | 4/1998 |
| WO | 98-29057 | 7/1998 |
| WO | 99/12483 | 3/1999 |
| WO | 99-33414 | 7/1999 |
| WO | 99-40964 | 8/1999 |
| WO | 99-47075 | 9/1999 |
| WO | 00-41652 | 7/2000 |
| WO | 00/47136 | 8/2000 |
| WO | 00-47139 | 8/2000 |
| WO | 01-49213 | 7/2001 |
| WO | 01-54625 | 8/2001 |
| WO | 01-62189 | 8/2001 |
| WO | 01-97115 | 12/2001 |
| WO | 02/41789 | 5/2002 |
| WO | 02-43620 | 6/2002 |
| WO | 02-47575 | 6/2002 |
| WO | 02/060352 | 8/2002 |
| WO | 02-036048 | 10/2002 |
| WO | 03-028592 | 4/2003 |
| WO | 03/030776 | 4/2003 |
| WO | 03-0285952 | 4/2003 |
| WO | 03-037227 | 5/2003 |
| WO | 03-094793 | 11/2003 |
| WO | 2004/019825 | 3/2004 |
| WO | 2004-058106 | 7/2004 |
| WO | 2004-089250 | 10/2004 |
| WO | 2004-089253 | 10/2004 |
| WO | 2004-093728 | 11/2004 |
| WO | 2004-105651 | 12/2004 |
| WO | 2005-002466 | 1/2005 |
| WO | 2005-004753 | 1/2005 |
| WO | 2005/004753 | 1/2005 |
| WO | 2005-009285 | 2/2005 |
| WO | 2005-011534 | 2/2005 |
| WO | 2005-011535 | 2/2005 |
| WO | 2005-023155 | 3/2005 |
| WO | 2005-027790 | 3/2005 |
| WO | 2005-046528 | 5/2005 |

OTHER PUBLICATIONS

Louise Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Peter C. Block, et al, "Percutaneous Approaches to Valvular Heard Disease," Current Cardiology Reports (United States), Mar. 2005, pp. 108-113.

Georg Lutter, et al, "Percutaneous Valve Replacement: Current State and Future Prospects." Annals of Thoracic Surgery (Netherlands), Dec. 2004, pp. 2199-2206.

Sachin Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Younes Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Younes Boudjemline, et al, "Images in Cardiovascular Medicine. Percutaneous Aortic Valve Replacement in Animals," Circulation (United States), Mar. 16, 2004, 109, p. e161.

Younes Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

S. Khambadkone, et al, "Percutaneous Implantation of Pulmonary Valves," Expert Review of Cardiovascular Therapy (England), Nov. 2003, pp. 541-548.

G. O. Yonga, et al, "Percutaneous Transvenous Mitral Commissurotomy in Juvenile Mitral Stenosis," East African Medical Journal (Kenya), Apr. 2003, pp. 172-174.

Younes Boudjemline, et al, "Transcatheter Reconstruction of the Right Heart," Cardiology in the Young (England), Jun. 2003, pp. 308-311.

Y. Boudjemline, et al, "Percutaneous Valve Insertion: A New Approach," Journal of Thoracic and Cardiovascular Surgery (United States), Mar. 2003, pp. 741-742.

Sachin Khambadkone, et al, "Percutaneous Pulmonary Valve Implantation: Early and Medium Term Results," Circulation 108 (17 Supplement), Oct. 28, 2003, p. IV-375.

Sachin Khambadkone, et al, "Percutaneous Pulmonary Valve Implantation: Impact of Morphology on Case Selection," Circulation 108 (17 Supplement), Oct. 28, 2003, p. IV-642-IV-643.

Y. Boudjemline, et al, "Percutaneous Implantation of a Valve in the Descending Aorta in Lambs," European Heart Journal (England), Jul. 2002, pp. 1045-1049.

Y. Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.

Philipp Bonhoeffer, et al, "Percutaneous Insertion of the Pulmonary Valve," Journal of the American College of Cardiology (United States), May 15, 2002, pp. 1664-1669.

(56) References Cited

OTHER PUBLICATIONS

Younes Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Younes Boudjemline, et al, "Steps Toward Percutaneous Aortic Valve Replacement," Circulation (United States), Feb. 12, 2002, pp. 775-778.

Y. Boudjemline, et al, "The Percutaneous Implantable Heart Valve," Progress in Pediatric Cardiology (Ireland), 2001, pp. 89-93.

Y. Boudjemline, et al, "Percutaneous Aortic Valve Replacement: Will We Get There?" Heart (British Cardiac Society) (England), Dec. 2001, pp. 705-706.

Y. Boudjemline, et al, "Percutaneous Implantation of a Biological Valve in Aortic Position: Preliminary Results in a Sheep Study," European Heart Journal 22, Sep. 2001, p. 630.

Y. Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

P. Bonhoeffer, et al, "Technique and Results of Percutaneous Mitral Valvuloplasty With the Multi-Track System," Journal of Interventional Cardiology (United States), 200, pp. 263-268.

P. Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

P. Bonhoeffer, et al, "Transcatheter Implantation of a Bovine Valve in Pulmonary Position: A Lamb Study," Circulation (United States), Aug. 15, 2000, pp. 813-816.

Z. Saliba, et al, "Treatment of Obstructions of Prosthetic Conduits by Percutaneous Implantation of Stents," Archives des Maldies du Coeur et des Vaisseaux (France), 1999, pp. 591-596.

P. Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.

G. O. Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

G. O. Yonga, et al, "Percutaneous Balloon Mitral Valvotomy: Initial Experience in Nairobi Using a New Multi-Track Catheter System," East African Medical Journal (Kenya), Feb. 1999, pp. 71-74.

G. O. Yonga, et al, "Percutaneous Transluminal Balloon Valvuloplasty for Pulmonary Valve Stenosis: Report on Six Cases," East African Medical Journal (Kenya), Apr. 1994, pp. 232-235.

Georg Lutter, et al, "Percutaneous Aortic Valve Replacement: An Experimental Study. I. Studies on Implantation," The Journal of Thoracic and Cardiovascular Surgery, Apr. 2002, pp. 768-776.

Bailey, "Percutaneous expandable prosthetic valves," In: Topol, EJ, ed. Textbook of Interventional Cardiology. vol. II. Second edition. WB Saunders, Philadelphia, 1994:1268-1276.

Babaliaros, et al., "State of the Art Percutaneous Intervention for the Treatment of Valvular Heart Disease: A Review of the Current Technologies and Ongoing Research in the Field of Percutaneous Valve Replacement and Repair," Cardiology 2007;107:87-96.

Block, et al., "Percutaneous Approaches to Valvular Heart Disease," Current Cardiology Reports, vol. 7, pp. 108-113 (2005).

Brodsky, "Percutaneous approaches to aortic valve replacement," Applications in Imaging—Cardiac Interventions, Dec. 2004, pp. 4-9.

Cribier, et al., "Percutaneous Implantation of Aortic Valve Prosthesis in Patients with Calcific Aortic Stenosis: Technical Advances, Clinical Results and Future Strategies," Journal of Interventional Cardiology, vol. 19, No. 5, Supplement 2006, pp. S87-S96.

Hanzel, et al., "Complications of percutaneous aortic valve replacement: experience with the Cribier-Edwards™ percutaneous heart valve," EuroIntervention Supplements (2006), 1 (Supplement A) A3-A8.

Khambadkone, et al., "Pediatric and Congenital Heart Disease," Catheterization and Cardiovascular Interventions 62:401-408 (2004).

Khambadkone, et al., "Percutaneous Pulmonary Valve Implantation in Humans Results in 59 Consecutive Patients," Circulation, 2005;112:1189-1197.

"New Frontiers in Heart Valve Disease," Medtech Insight, vol. 7, No. 8 (Aug. 2005).

Palacios, "Percutaneous Valve Replacement and Repair, Fiction or Reality?" Journal of the American College of Cardiology, vol. 44, No. 8, 2004 pp. 1662-1663.

Ruiz, "Transcathether Aortic Valve Implantation and Mitral Valve Repair: State of the Art," Pediatric Cardiology, 26:289-294, 2005.

Huber, et al., "Do Valved Stents Compromise Coronary Flow?" Eur. J. Cardiothorac. Surg. 2004;25:754-759.

Ruiz, et al., "Transcatheter placement of a low-profile biodegradable pulmonary valve made of small intestinal submucosa: A long-term study in a swine model," J. of Thoracic and Cardiovascular Surgery, vol. 130, No. 2, Aug. 2005, 477.e1-477e9.

Chiam, et al., "Percutaneous Transcatheter Aortic Valve Implantation: Assessing Results, Judging Outcomes, and Planning Trials," JACC: Cardiovascular Interventions, vol. 1, No. 4, Aug. 2008:341-50.

* cited by examiner

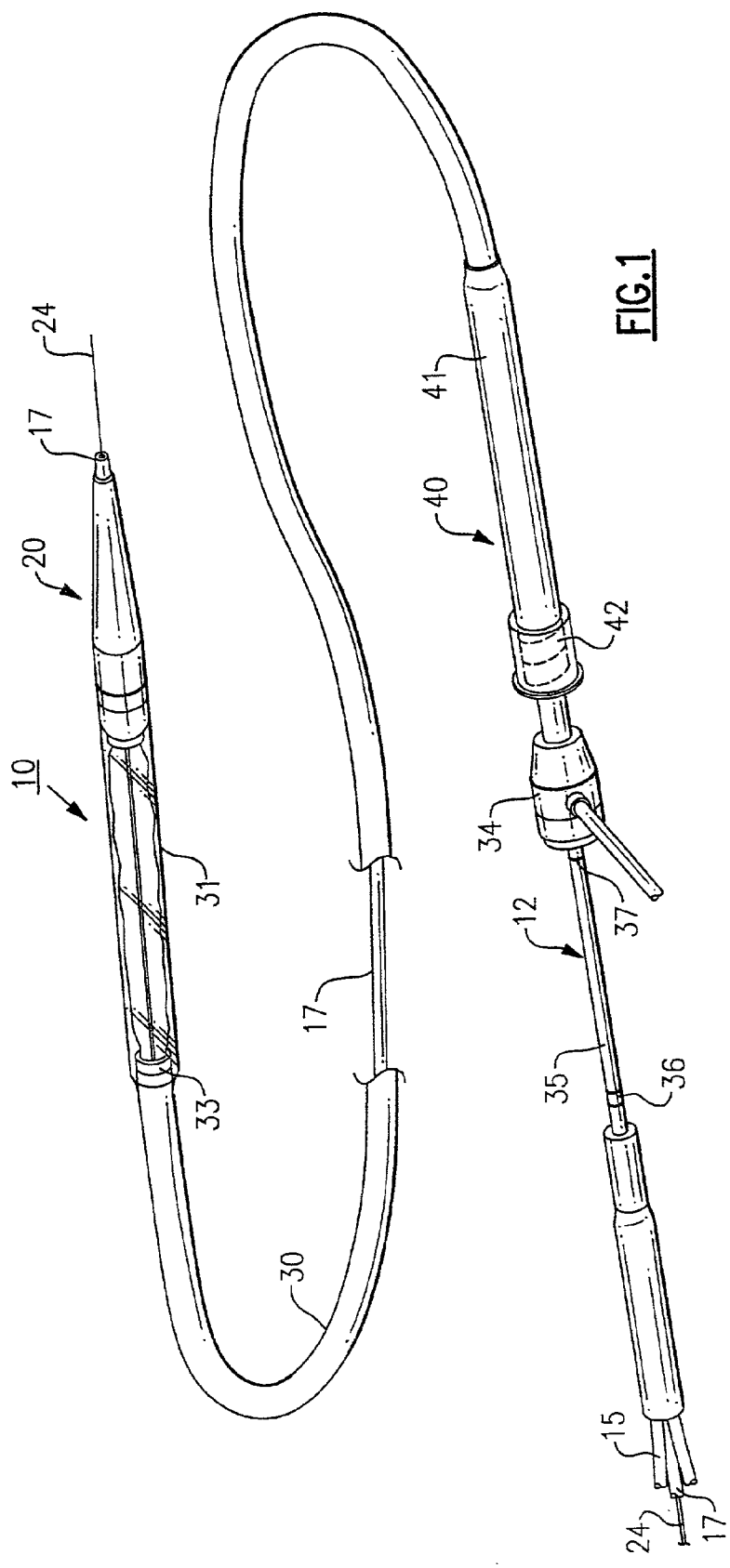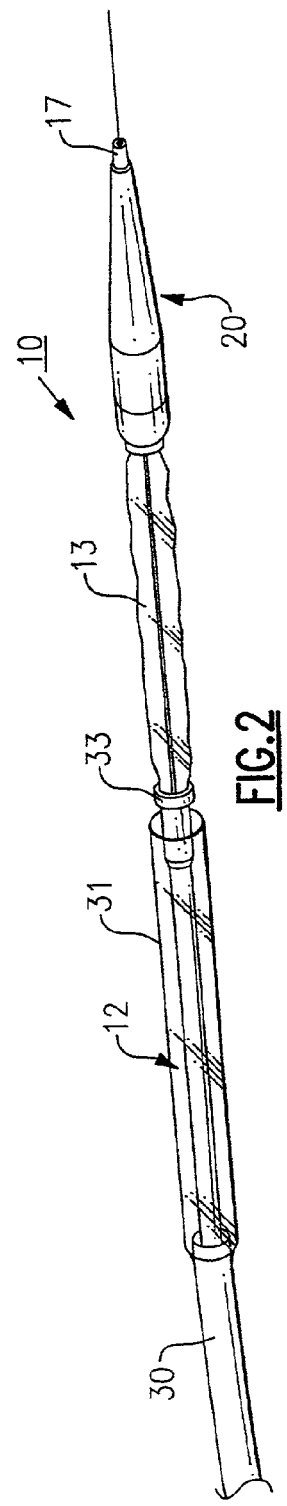

SYSTEM FOR IMPLANTING A REPLACEMENT VALVE

FIELD OF THE INVENTION

This invention relates to a system for the percutaneous implantation of a biological venous valvular replacement for a human valve.

BACKGROUND OF THE INVENTION

There exists a need in the medical field for an improved system for carrying out the percutaneous implantation of biological venous valvular replacements for human valves and in particular cardiac valves. Up until recently, many valves such as heart valves had to be replaced surgically. Accordingly, the patients were exposed to all the potential dangers of major surgery.

Recently, procedures have been devised for implanting biological valves harvested from animals percutaneously into humans to replace damaged or malfunctioning valves. Andersen et al. in U.S. Pat. No. 5,840,081 describes a system for carrying out such a procedure. In Andersen et al., a biological cardiac valve is mounted upon the expandable stent of a catheter. The assembly is crimped onto the balloon section of the catheter and a protective cap is placed over the package. The catheter is then passed through a body lumen into a predetermined site within the heart. The package is then moved out of the cap and is positioned in the implantation site using well known positioning techniques. The balloon is inflated causing the stent with the replacement valve attached thereto to expand thus implanting the valve within the desire site.

The Andersen et al. type system works well in practice in that it can be carried out in a relatively short period of time when compared to surgical procedures and the risk to the patient is considerably reduced. However, the biological prosthesis that include the venous valvular replacement and the stent tends to be relatively bulky and thick even when tightly compressed against the deflated balloon and thus sometimes difficult to move through the body lumen into the implantation site. Most catheters in present day use can not deliver the necessary torque to guide the prosthesis through the body lumen, particularly where there is a relatively tight bend in the path of travel. In addition, most of the catheters that are equipped with protective caps do not possess the rigidity needed to hold the prosthesis in the desired location as the balloon is cleared for inflation.

SUMMARY OF THE INVENTION

It is therefore an object of the present invention to improve percutaneous delivery systems for placing a biological venous valvular replacement for a defective valve within an implantation site.

A further object of the present invention is to improve the steerability of a balloon catheter used to implant a biological valve percutaneously in a patient.

A still further object of the present invention is to more accurately place a biological valve prosthesis with a desired implantation site.

Another object of the present invention is to provide a more compact system for percutaneously inserting a biological replacement valve into an implantation site.

These and other objects of the present invention are attained by a system for percutaneously inserting a biological venous valvular replacement for a defective valve within a patient through a body lumen. The system includes a balloon catheter upon which a collapsable stent containing a venous valvular replacement is mounted in a collapsed condition upon the deflated balloon. A protective shield is placed over the balloon and the replacement valve unit. The shield is movable from a closed position over the balloon to a fully opened position without having to axially displace the balloon so that the balloon can be inflated to expand the stent and accurately implant the replacement valve. A central lumen formed of a stainless steel tube passes through the catheter to provide a one to one torque ratio between the proximal end of the catheter and its distal end. The wall thickness of the venous valvular replacement is reduced from its original size by between 50% and 90% to provide for a more compact replacement package when the package is collapsed upon the uninflated balloon.

BRIEF DESCRIPTION OF THE DRAWING

For a better understanding of these and other objects of the invention, reference will be made to the following detailed description of the invention which is to be read in association with the accompanying drawing, wherein:

FIG. 1 is a perspective view illustrating a delivery system embodying the teachings of the present invention for the percutaneous insertion and implantation of a biological replacement valve within a patient;

FIG. 2. is a partial perspective view illustrating the distal end of the system shown in FIG. 1 with its protective shield moved back away from the balloon section of the system;

DETAILED DESCRIPTION OF THE INVENTION

Figure 4:
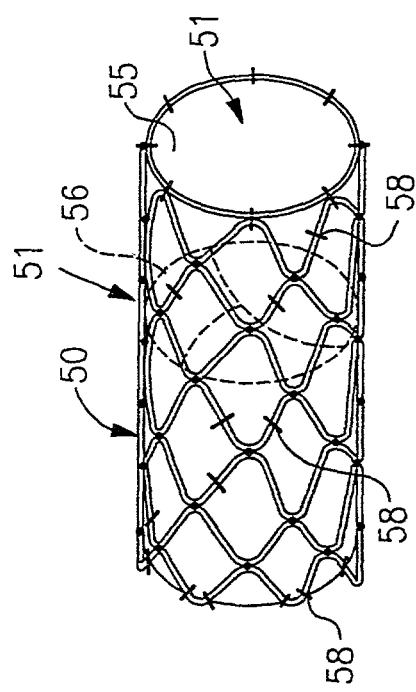
FIG. 4 is a perspective view of the stent with a biological replacement valve unit mounted inside the stent.

FIGS. 1 and 2 illustrate a system, generally referenced 10, for percutaneous insertion and implantation of a biological venous valvular replacement for a defective or malfunctioning valve. The system includes an elongated balloon catheter 12 having an inflatable balloon 13 joined to the distal end of the catheter. The balloon is connected in fluid flow communication with a lumen 15 through which the balloon is inflated or deflated in a manner well known in the art. Preferably the balloon is inflated using a radio-opaque fluid. Although a single balloon is shown in the present embodiment of the invention, it should be obvious to one skilled in the art that a plurality of balloons in various configurations may be employed in the practice of the present invention.

The catheter further includes a centrally located lumen 17 that passes through the entire length of the catheter from its proximal end to its distal end. The central lumen, unlike other catheter lumens employed in the prior art, is formed from a length of stainless steel tubing. A pointed nose cone 20 is affixed to the distal end of the tubing and the rear section 21 of the nose cone is secured to the front part of the balloon. The distal end of the central lumen 17 opens to the surrounding ambient at one end through the front of the nose cone and at the other end through the rear section of the catheter as illustrated in FIG. 1.

A thin guide wire 24 passes through the central lumen which is used in a conventional manner to guide the catheter into the implantation site.

It has been found that when a stent containing a biological valve is mounted upon the balloon of a catheter, the package tends to become overly large and clumsy to maneuver. Accordingly, maneuvering of the catheter through a vein or artery to the implantation site becomes difficult, particularly where the catheter has to be conducted through a number of bends along the intended path of travel. Conventional catheters and the lumens running there-through are fabricated from plastic materials that tend to twist when a torque is applied to the proximal or steering end of the device. This twisting adversely effects the steering control at the distal end of the catheter making it difficult to direct the catheter around any bends in the intended path of travel and accurately place the replacement package in the implantation region. The stainless steel tube running down the center of the present catheter is designed to provide the catheter with a 1 to 1 torque ratio between the proximal end of the catheter and its distal end. This in turn, enhances the steerability of the catheter as well as providing the user with the ability to more easily push the catheter along the desired path of travel. It has been found that a stainless steel tube having an inside diameter of about 0.039" will provide the above noted desired properties while at the same time providing the catheter with sufficient flexibility to pass readily through bent regions along the path of travel. This, along with the contoured nose cone, enables the user to rapidly guide the catheter into a desired implantation site and thus considerably shorten the implantation procedure when compared to similar systems used in the art.

An elongated sheath 30 is placed over the catheter. A close running fit is provided between the sheath and the catheter so that the sheath can slide easily over the body of the catheter. A protective shield 31 is attached to the distal end of the sheath so that the shield can be repositioned by simply moving the sheath over the catheter. In assembly, the shield is movable between a fully closed position as illustrated in FIG. 1 wherein the balloon and the replacement package are protectively enclosed and a fully opened position as illustrated in FIG. 2 wherein the balloon is cleared for inflation. An annular stop 33 is mounted on the catheter adjacent to the back edge of the balloon section. The stop is arranged to arrest the forward motion of the sheath once the shield reaches a fully closed position insuring that the shield will not ride over the nose cone.

The proximal end of the sheath contains a cylindrical flange 34 by which aids the operator to manually slide the sheath over the catheter body to open or close the protective shield. The distal end 35 of the catheter passes out of the sheath through the flange and extend back a distance that is greater than the axial length of the shield. Indicator marks 36 and 37 are placed on the extended length of the catheter for informing the operator when the shield is located in either the open or the closed position.

A cylindrical fluid barrier 40 is slidably mounted upon the proximal end of the sheath. The barrier includes a tubular body section 41 and a radially extended end flange 42. The outside diameter of the body section is about equal to that of the protective shield. In practice, once the balloon shield has passed into the body lumen through the physician's incision, the body of the fluid barrier is passed into the body lumen through the incision and the flange is placed in contact against the incision opening. Once inserted, the barrier restricts the flow of body fluid through the incision opening while, at the same time, allowing the sheath and the catheter to be advanced and maneuvered within the body lumen into the implantation site.

As will be further explained below, the prosthetic device made up of an expandable stent and a biological venous valvular replacement is mounted in a collapsed state upon the balloon section of the catheter. The replacement is preferably has been harvested from the jugular vein of an animal, such as a cow, and is secured to the inside of the stent. Initially, the sheath is pulled back along the catheter to expose the collapsed balloon and the prosthetic device is passed over the balloon and crimped tightly onto the balloon to establish a compact low profile package. The sheath is then moved forward along the catheter to place the shield over the package to protect it during insertion. Once the package is positioned within the insertion site the shield again is moved back over the stationary body of the catheter as explained above and the balloon is inflated to implant the biological replacement within the site.

Figure 3:
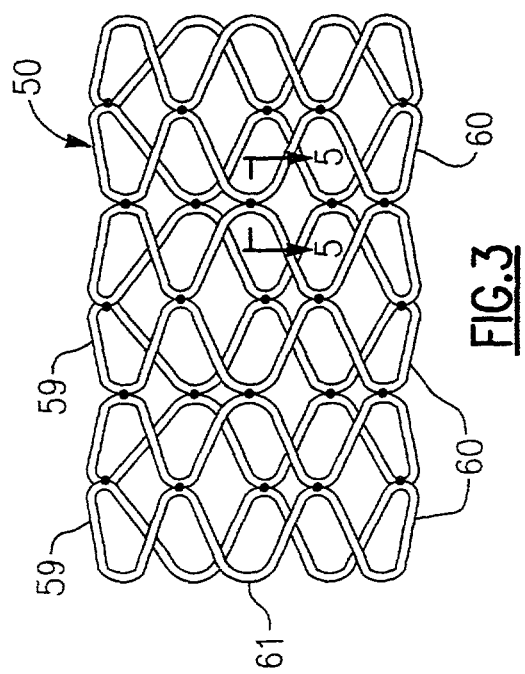
FIG. 3 is an enlarged side elevation of an expanded stent used in the practice of the present invention.

Turning more specifically to FIGS. 2-5, there is illustrated a stent 50 that is particularly well suited for use in the present system. A biological venous valvular replacement 51 for a defective valve is carried inside of the stent. Although the present valve replacement is ideally suited for percutaneous implantation of a pulmonary valve, it should clear that the present system can be used in a number of similar applications without departing from the teachings of the invention. As illustrated in FIG. 3, the biological replacement unit 51 includes a section of vein 55 that contain a valve 56. As will be explained below in further detail the venous valvular replacement is attached to the stent by means of sutures 58.

The present expandable stent includes a series of fine wire ribbon sections, each designated 60 that are joined together to create a tubular or cylindrical member. The wire stand 59 of each section is fabricated of a soft, highly malleable metal alloy that has been fully annealed to remove as much of its spring memory as possible. Preferably the wire material is fabricated of an alloy consisting of about 90% platinum and 10% iridium that has a tensile strength of between 150,000 psi and 175,000 psi. Although a platinum iridium wire is preferred for use in the present stent, other alloys having similar properties such as a gold nickel alloy may also be employed. Prior to winding the wire ribbon sections into a cylindrical shape, each section is formed so that it contains a series of alternating sinusoidal bends 61. The sections are formed by winding the strand of wire between rows of vertical pins projecting from the surface of a flat substrate. The strand is then wound about the pins in alternate rows to create a sinusoidal shaped ribbon section having a desired number of bends and a free length of wire is located at each end of the ribbon section.

Each ribbon section is next wound into a cylinder and the cylinders are then placed in axial alignment so that the apex of each bend section is located in close proximity with the apex of a bend section on an adjacent ribbon section. The adjacent bends are then welded together to cojoin the ribbon section in assembly. Although not shown, the free ends of the adjacent cylindrical ribbon sections, in turn, are bent into parallel overlapping alignment and are cojoined using similar welds.

Figure 5:
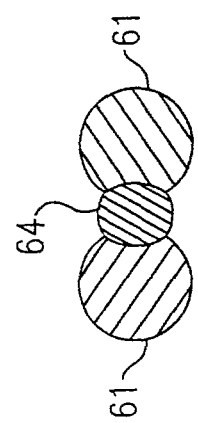
FIG. 5 is an enlarged section taken along lines 4-4 in FIG. 2.

Referring to FIG. 5, there is illustrated a typical weld joint 64 used in the practice of the present invention. Each weld is formed so that it lies inside the boundaries of the cylindrical stent as described by the inside diameter and outside diameter of the stent. Accordingly, the welds do not protrude beyond the boundaries of the wire cylinder into regions where rough edges of the welds might come in contact with the tissue of the biological valve replacement thereby preventing the tissue from becoming damaged during insertion and implantation.

A stent of the construction and configuration as herein described has extremely good flexibility, dimensional stability, very smooth surfaces, a low profile when collapsed and an immunity to fatigue and corrosion. As should be evident the length of the stent can be varied by varying the number of ribbon sections that are utilized. By the same token, the working range of the stent between its fully collapsed condition and it fully expanded condition can also be varied by varying the number of bends in each of the ribbon sections. As can be seen each stent can be tailored for insertion into a particular body site to provide for the most effective implantation of the biological valve which is attached to the stent.

Because of the stent construction there is very little or no axial deformation of the stent as it is radially expanded or collapsed. Another feature of the present stent is its ability to be reconfigured even after implantation without adversely effecting the stents performance. This feature is important in cases where a valve has been implanted in a growing child. Rather than replacing a valve periodically during the growth period, the supporting stent can be simply reconfigured to accommodate for growth using a percutaneously introduced balloon catheter for re-engaging the stent to reconfigure the stent so that it will conform to the changes in the implantation site produced by growth.

Figure 6:
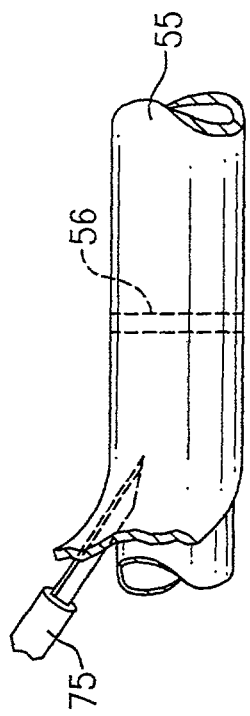
FIG. 6 is a side elevation illustrating a biological replacement valve suitable for use in the present invention as the wall thickness of the vein which supports the valve is being reduced.

As illustrated in FIG. 4, the stent is initially expanded to a desired diameter which generally conforms to the body vessel configuration at the implantation site. Next, as illustrated in FIG. 6, the vein section of the valve is trimmed to a desired length conforming to the length of the stent with the valve 56 being located in about the mid-region of the stent. In addition, the wall of the vein 56 is reduced in thickness to between 50% to 90% of its original thickness to considerably reduce the size of the valve package when the stent is collapsed over the balloon prior to insertion. It has been found that the jugular vein of a bovine animal is formed by layers of tissue that can be readily peeled back using a sharp instrument 75. The layers can be removed without destroying the integrity of the vein structure or its ability to function in a replacement prosthesis. The wall of the vein is trimmed so that its outside diameter about matches the inside diameter of the expanded stent. The vein is then passed into the expanded stent and the vein sutured to the stent as illustrated in FIG. 3. The sutures are arranged to support the vein in a fully opened circular configuration within the expanded stent.

Once the prosthesis has been sutured in place, it is passed over the balloon section of the catheter and the stent is collapsed tightly against the balloon to provide a more compact than normal package that can more easily be delivered through a body lumen into an implantation site when compared to similar devices employing bovine or eqvine biological valves replacements.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A delivery system for percutaneously implanting a heart valve assembly at an implantation site within a patient, the delivery system comprising:
   an elongated catheter;
   a stop on the elongated catheter;
   a tip at a distal end of the elongated catheter;
   a sheath configured to slidably receive the elongated catheter; and
   a protective shield at a distal end of the sheath;
   wherein the sheath and protective shield are moveable relative to the elongated catheter and the stop between a first dosed position with a distal end portion of the protective shield being engaged with a proximal end portion of the tip and the heart valve assembly being positioned between the protective shield and the elongated catheter, and a second open position with the protective shield being sufficiently spaced from the heart valve assembly to permit expansion of the heart valve assembly; and
   wherein the stop is positioned on the elongated catheter and sized such that at the first dosed position the stop abuts a distal end of the sheath to stop motion of the sheath and the protective shield relative to the elongated catheter and to prevent the protective shield from overlapping the tip.

2. The delivery system of claim 1, wherein the stop is an annular shoulder extending radially outward from the elongated catheter.

3. The delivery system of claim 1, further comprising an inflatable balloon coupled to the elongated catheter and expandable between a collapsed position at which the heart valve assembly is crimped on the inflatable balloon and capable of being transported by the catheter to an implantation site, and an expanded position for implanting the heart valve assembly at the implantation site.

4. The delivery system of claim 3, wherein the stop abuts a proximal edge portion of the inflatable balloon.

5. The delivery system of claim 3, wherein the balloon and protective shield are sized and shaped to afford crimping of the heart valve assembly onto the balloon so that the heart valve assembly may be positioned between the balloon and the shield.

6. The delivery system of claim 1, wherein the tip is a contoured nose cone configured to slide along an internal surface of a blood vessel.

7. The delivery system of claim 6, wherein the contoured nose cone comprises a leading tip portion having a diameter that increases in a proximal direction.

8. The delivery system of claim 7, wherein the leading tip portion is substantially frusto-conical.

9. The delivery system of claim 1, wherein the tip has a profile that radially extends beyond the heart valve assembly crimped on an inflatable balloon coupled to the elongated catheter.

10. The delivery system of claim 1, wherein the elongated catheter and the tip collectively define a passageway for slidably receiving a guide wire.

* * * * *

UNITED STATES PATENT AND TRADEMARK OFFICE
CERTIFICATE OF CORRECTION

| | | |
|---|---|---|
| PATENT NO. | : 8,721,713 B2 | Page 1 of 1 |
| APPLICATION NO. | : 10/127969 | |
| DATED | : May 13, 2014 | |
| INVENTOR(S) | : Tower et al. | |

It is certified that error appears in the above-identified patent and that said Letters Patent is hereby corrected as shown below:

In the claims

In column 6, line 13 (claim 1), "first dosed position" should read -- first closed position --.

In column 6, line 21 (claim 1), "first dosed position" should read -- first closed position --.

Signed and Sealed this
Fifteenth Day of July, 2014

Michelle K. Lee
*Deputy Director of the United States Patent and Trademark Office*